(12) United States Patent
Liu et al.

(10) Patent No.: US 8,790,663 B2
(45) Date of Patent: Jul. 29, 2014

(54) ANTIGENIC DETERMINANTS OF HUMAN DEATH RECEPTOR DR5

(75) Inventors: Yanxin Liu, Beijing (CN); Peng Zhang, Beijing (CN); Yong Zheng, Toronto (CA); Dexian Zheng, Beijing (CN)

(73) Assignee: Institute of Basic Medical Sciences, Chinese Academy of Medical Sciences (CN)

( * ) Notice: Subject to any disclaimer, the term of this patent is extended or adjusted under 35 U.S.C. 154(b) by 105 days.

(21) Appl. No.: 13/257,156

(22) PCT Filed: Apr. 3, 2009

(86) PCT No.: PCT/CN2009/071164
§ 371 (c)(1),
(2), (4) Date: Dec. 2, 2011

(87) PCT Pub. No.: WO2010/111842
PCT Pub. Date: Oct. 7, 2010

(65) Prior Publication Data
US 2012/0271034 A1    Oct. 25, 2012

(51) Int. Cl.
*C07K 7/06* (2006.01)
*C12N 5/16* (2006.01)
*C12N 15/12* (2006.01)
*C07K 14/705* (2006.01)

(52) U.S. Cl.
USPC ............... 424/277.1; 424/185.1; 435/334; 435/344; 530/300; 536/23.1

(58) Field of Classification Search
CPC .................................................. C07K 2317/34
See application file for complete search history.

(56) References Cited

U.S. PATENT DOCUMENTS

| | | | |
|---|---|---|---|
| 5,238,921 A * | 8/1993 | Maruyama et al. | |
| 6,313,269 B1 * | 11/2001 | Deen et al. | |
| 7,893,216 B2 * | 2/2011 | Liu et al. | |
| 8,178,503 B2 * | 5/2012 | Rigoutsos et al. | |
| 2009/0226438 A1 * | 9/2009 | Gliniak et al. | |

FOREIGN PATENT DOCUMENTS

| | | |
|---|---|---|
| CN | 1275162 | 11/2000 |
| CN | 1610696 | 4/2005 |
| CN | 1635908 | 7/2005 |
| CN | 1673232 A | 9/2005 |
| CN | 1239516 C | 2/2006 |
| CN | 101074261 | 11/2007 |
| CN | 101300273 | 11/2008 |

OTHER PUBLICATIONS

Walczak et al., TRAIL-R2: a novel apoptosis-mediating receptor for TRAIL, EMBO J. 16(17):5386-5397, Sep. 1, 1997.*
Guo et al., A novel anti-human DR5 monolconal antibody with tumoricidal activity induces caspase-dependent and caspase-independent cell death, J. Biol. Chem. 280(51):41940-41952, Dec. 23, 2005.*
Zhang et al., Targeting a novel N-terminal epitope of death receptor 5 triggers tumor cell death, J. Biol. Chem. 285(12):8953-8966 and Supplemental Data, Mar. 19, 2010.*
"Certificate of Biomaterial Deposit and Viability, CGMCC Deposit No. 2938", Deposited by Institute of Basic Medical Sciences, Chinese Academy of Medical Sciences; Deposited with China General Microbiological Culture Collection Center, (Mar. 20, 2009), 2 pgs.
"Certificate of Biomaterial Deposit and Viability, CGMCC Deposit No. 2939", Deposited by Institute of Basic Medical Sciences, Chinese Academy of Medical Sciences; Deposited with China General Microbiological Culture Collection Center, (Mar. 20, 2009), 2 pgs.
"International Application No. PCT/CN2009/071164, International Search Report mailed Jan. 7, 2010", (Jan. 7, 2010), 18 pgs.

* cited by examiner

*Primary Examiner* — Claire Kaufman
(74) *Attorney, Agent, or Firm* — Schwegman, Lundberg & Woessner, P.A.

(57) ABSTRACT

Provided are antigenic determinants of human death receptor DR5. The antigenic determinants have the amino acid sequence of LITQQDLAPQQRA (SEQ ID No. 7), wherein the core polypeptide is QDLAP (SEQ ID No. 1). The polypeptides comprising said antigenic determinants can activate the signal pathway downstream of DR5 after binding to monoclonal antibody AD5-10, then result in apoptosis. The antigenic determinants can be used for screening and preparing anti-human DR5 agonistic antibody, small molecular compound binding to DR5 and DR5 vaccine.

3 Claims, 6 Drawing Sheets

Fig. 4
A
AD5-10
B
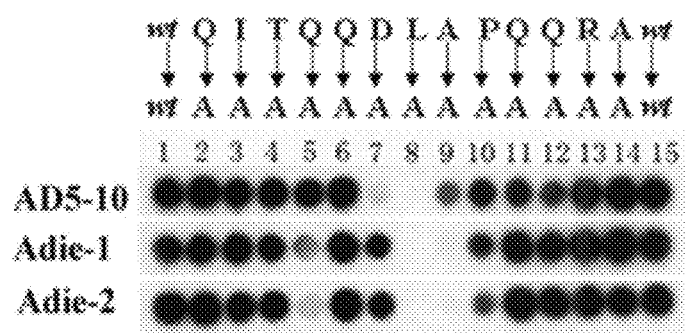
C
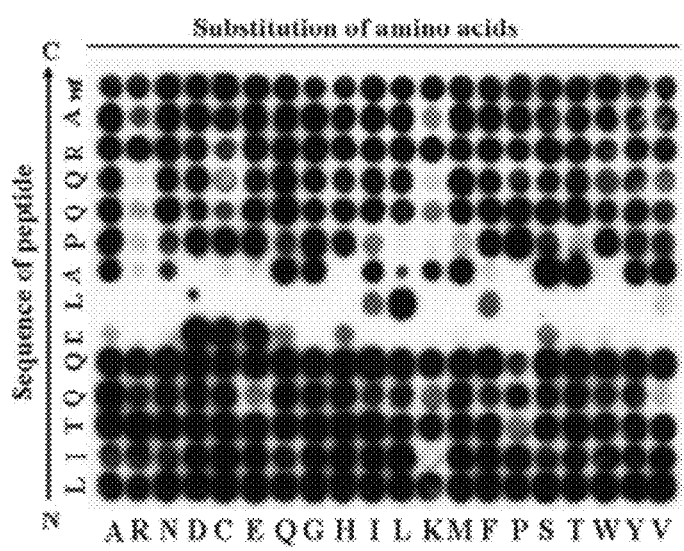

Fig. 6
*Extracellular domain  TM  intracellular domain  FLAG-tag*
AD5-10 
anti-FLAG 
anti-GAPDH 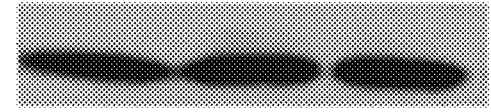

US 8,790,663 B2

ANTIGENIC DETERMINANTS OF HUMAN DEATH RECEPTOR DR5

PRIORITY CLAIM TO RELATED APPLICATIONS

This application is a national stage application under 35 U.S.C. §371 of PCT/CN2009/071164, filed Apr. 3, 2009, and published as WO 2010/111842 A1 on Oct. 7, 2010, which application and publication are incorporated herein by reference and made a part hereof in their entirety, and the benefit of priority of each of which is claimed herein.

FIELD OF THE INVENTION

This present invention provides a core peptide sequence identified by a peptide array, which is highly homologous to amino acid residues 4 to 16 within the N-terminal region of the death receptor 5 (DR5) of human tumor necrosis factor-related apoptosis inducing ligand (TRAIL), and moreover, which is an antigenic determinant (epitope) recognized by AD5-10 (Chinese patent number ZL02104519.4). Furthermore, this present invention relates to the uses of the epitope and derivatives thereof in the preparation of the agonistic anti-DR5 monoclonal antibody, the small molecular compounds binding to DR5, preventive vaccines or therapeutic vaccines. At last, this present invention relates to the uses of the anti-sense nucleotides and small molecular ribonucleotides of the epitope and derivatives thereof in the treatment and prevention of diseases associated with cancers and/or AIDS.

BACKGROUND OF THE INVENTION

Death receptors are tumor necrosis factor receptor (TNFR) gene superfamily members, of which the structural characteristics are of a cysteine-rich extracellular domain (ECD) and an intracellular death domain (DD). Tumor necrosis factor-related apoptosis inducing ligand (TRAIL) is a natural ligand for death receptors DR4 and DR5 and can activate the death receptor pathway and mitochondrion pathway of apoptotic cell death by engaging the death receptors, thereby inducing the apoptotic cell death of cells. TRAIL has a killing activity on multiple kinds of tumors while has no toxic and side effects on most normal cells. In addition, Human Immunodeficiency Virus (HIV)-infected T lymphocytes are more sensitive to the cytotoxicity effect mediated by TRAIL and the receptors thereof. These study results indicate that TRAIL and the receptors thereof can be of an attractive perspective in the treatment of cancers and AIDS.

Five natural receptors for TRAIL have been identified, including DR4 (Death Receptor 4, TRAIL-R1), DR5 (Death Receptor 5, TRAIL-R2), DcR1 (Decoy Receptor 1, TRID, TRAIL R3), DcR2 (Decoy Receptor 2, TRUNDD, TRAIL R4), and osteoprotegerin (OPG). Where, TRAIL DR4 and DR5 are capable of delivering the apoptosis signal mediated by TRAIL since they both comprise an integrate extracellular domain and intracellular domain; while decoy receptors DcR1 and DcR2 lack an intracellular domain or their intracellular domains are incomplete and can not deliver the apoptosis signal mediated by TRAIL; OPG is a secreted receptor capable of inhibiting osteoclasts and increasing bone density of which the expression in the transgenic mice model can result in a splenomegalia. OPG can inhibit the binding of TRAIL with the death receptor so as to regulate TRAIL induced apoptotic cell death. Thus, OPG is a soluble "decoy" receptor of TRAIL. In sum, all decoy receptors can compete for binding of TRAIL with DR4 and DR5 and block TRAIL-mediated apoptotic cell death.

Prior studies indicate that the expressions of death receptors DR4 and DR5 present in both human normal tissues and malignant tissues and the expression in malignant tissues is often higher. Decoy Receptor DcR1 is usually expressed in normal human tissues (transcripts thereof present in peripheral blood lymphocytes (PBL), spleen, lung, placenta, osseous tissue, prostate, thymus, testis, large intestine, small intestine and ovary), wherein the expressions in peripheral blood lymphocytes and spleen are higher, but the expressions in cancer cells and transformed cells are absent or very low; DcR2 is expressed in many normal tissues, especially the expressions in fetal liver tissues and adult testis tissues are higher, suggesting the protective role of DcR2 on these tissues. DcR2 is not expressed in the overwhelming majority of tumor cells.

Just due to the asymmetry of the distribution of death receptors in normal tissues and tumor tissues, TRAIL can specifically kill many tumor cells while have no cytotoxicity to most normal cells. Thus, it is a hot spot in the current biomedicine field to use TRAIL to induce the apoptotic cell death of tumor cells thereby specifically treating tumors. However, after many studies in depth, it is found that some cancer cell lines show resistance to TRAIL-induced apoptotic cell death, while the agonist monoclonal antibodies specifically against death receptors are more specific and safe, offering a new hope for the treatment of cancers.

The studies indicate that the monoclonal antibodies against DR4 or DR5 have intense killing activity to tumor cells while have no cytotoxicity to normal cells. The epitopes recognized by the various monoclonal antibodies or single-chain antibodies against DR4 or DR5 reported in the literature are overlapping or partially overlapping with the TRAIL binding regions on the DR4 or DR5 molecules. Thus, most of these monoclonal antibodies can compete with TRAIL for binding with death receptors DR4 or DR5.

It is reported in the literature that the extracellular region of DR5 molecule has two binding sites to TRAIL (the binding site of high affinity and the binding site of low affinity) which lies in two cysteine-rich domains (CRD1 and CRD2) respectively. Although the monoclonal antibody AD5-10 disclosed in Chinese patent number ZL02104519.4 also target the extracellular region of DR5 molecule, the binding site thereof is different from those of the monoclonal antibodies reported in the literature and the binding of AD5-10 with DR5 does not affect the binding of TRAIL with DR5. Therefore, there is a synergistic effect between TRAIL and AD5-10 when inducing the apoptotic cell death of tumor cells.

SUMMARY OF THE INVENTION

The first aspect of the present invention is to provide a polypeptide and derivatives thereof comprising an amino acid sequence named as core peptide: QDLAP (SEQ ID No: 1), wherein the polypeptide and derivatives thereof share the same sequence with the amino acid residues 8 to 12 within the N-terminal region of death receptor DR5 or the polypeptide and derivatives thereof extend from the N-terminal of the said amino acid sequence to the C-terminal of the amino acid sequence in accordance with the amino acid sequence of DR5, and the extended amino acid sequences have the amino acid sequences selected from SEQ ID Nos: 3 to 8, and wherein the polypeptide and derivatives thereof comprise an epitope of human DR5 recognized by the monoclonal antibody AD5-10, wherein the sequences of SEQ ID No: 3 to 8 are as follows:

```
SEQ ID No: 3:  ESALITQQDLAP         (a.a. 1-12)
SEQ ID No: 4:  ALITQQDLAPQQ         (a.a. 3-14)
SEQ ID No: 5:  ITQQDLAPQQRA         (a.a. 5-16)
SEQ ID No: 6:  QQDLAPQQRAAP         (a.a. 7-18)
SEQ ID No: 7:  LITQQDLAPQQRA        (a.a. 4-16)
SEQ ID No: 8:  ESALITQQDLAPQQRAAP.  (a.a. 1-18)
```

The second aspect of the present invention is to provide a core peptide and derivatives thereof comprising the said core peptide above and having the following amino acid sequence formula $X_1X_2X_3X_4X_5\underline{DLA}X_6X_7X_8X_9X_{10}$ of SEQ ID No: 9, wherein:

$X_1$ is any amino acid residue, but not required if there is no specification, $X_2$ is any amino acid residue except for Lysine residue, $X_3$ is any amino acid residue, $X_4$ is any amino acid residue, $X_5$ is any amino acid residue, $X_4$ and $X_5$ can be the same or different, $X_6$ is any amino acid residue except for basic or branched-chain amino acid residue, $X_7$ is any amino acid residue except for basic amino acid residue, $X_8$ is any amino acid residue except for basic amino acid residue, $X_7$ and $X_8$ can be the same or different, $X_9$ is any amino acid residue, but not required if there is no specification, and $X_{10}$ is any amino acid residue, but not required if there is no specification.

The third aspect of the present invention is to provide a nucleotide sequence encoding for the said core peptide, which has the sequence of SEQ ID No: 2, wherein N is selected from A, T, C or G.

The paragraph beginning at page 3, line 43 is amended as follows: The fourth aspect of the present invention is to provide a method for preparing a monoclonal antibody inducing the apoptotic cell death of tumor cells, characterized in comprising the following steps:

1) Polypeptide sequence "C with LITQQDLAPQQRA (SEQ ID No:7)" is synthesized according to the sequence LITQQDLAPQQRA of (SEQ ID No:7 using QDLAP (SEQ ID No:1) as the core peptide, and then keyhole limpet hemocyanin is introduced to the N-terminal of polypeptide to obtain an immunopeptide, 2) Immunizing a mouse with the immunopeptide and fusing the splenocytes taken from the immunized mouse with SP2/0 myeloma cells to generate a hybridoma cell line, and then obtaining the monoclonal antibody hybridoma cells raised against the polypeptide by screening.

The fifth aspect of the present invention is to provide the hybridoma cell lines prepared according to the method as said in the fourth aspect of present application. Preferably, the said hybridoma cell lines which can generate apoptosis-inducing monoclonal antibodies are Adie-1 and Adie-2, which were deposited at China General Microbiological Culture Collection Center (CGMCC) on 20 Mar. 2009 with the deposit numbers 2938 and 2939, respectively; more preferably, the said hybridoma cell line is capable of generating monoclonal antibody Adie-1 or Adie-2 respectively.

The sixth aspect of the present invention is to provide the monoclonal antibodies produced with the said hybridoma cell lines as said in the fifth aspect of present invention. Preferably, the said monoclonal antibodies are Adie-1 or Adie-2.

The seventh aspect of the present invention is to provide uses of the core peptide and derivatives thereof as said above in the preparation of monoclonal antibodies binding to DR5.

The eighth aspect of the present invention is to provide uses of the core peptide and derivatives thereof in the screening of small molecular compounds that can bind to DR5 and can be used in the treatment of tumors and/or AIDS.

The ninth aspect of the present invention is to provide uses of the core peptide and derivatives thereof in the preparation of vaccines for the prevention or treatment of tumors and/or AIDS.

The tenth aspect of the present invention is to provide uses of the nucleotide sequences according to the third aspect of present invention in the preparation of the anti-sense nucleotides and small molecular ribonucleotides for the treatment and/or prevention of cancers and/or AIDS.

The eleventh aspect of the present invention is to provide uses of the said monoclonal antibodies according to the sixth aspect of present invention in the preparation of an anti-tumor and/or anti-AIDS medicament.

In another word, the present invention relates to an amino acid sequence of a polypeptide, or named as the core peptide, of which the amino acid sequence is QDLAP (SEQ ID No: 1).

Term: the said amino acid sequence of the core peptide generally refers to polypeptides whose sequences are based on QDLAP (SEQ ID No: 1).

The present invention is accomplished by using Oriented Peptide Array Library (OPAL) and on the basis of the chemical synthesis of the "overlapping" peptide pool of human death receptor DR5 (NCBI Acc#: NP_671716.1) and by combining the molecular biology and cell biology approaches.

In detail, this present invention screened out a core peptide by utilizing a polypeptide array library, of which the amino acid sequence is 100% identical to the non-CRD domain of the extracellular region of known human death receptor DR5 molecule. Monoclonal antibodies raised against the polypeptides comprising the said sequence possess a capability for inducing the apoptotic cell death of tumor cells, suggesting the tight functional relationship between the function of the said peptide sequence and the human death receptor DR5 molecule, and suggesting that the N-terminal linear sequence of DR5 receptor may have the potentiality to cause the conformational change of the DR5 molecule and the ability to recruit the intracellular signal molecules. Furthermore, the further studies find that the mouse anti-human death receptor DR5 monoclonal antibody AD5-10 (Chinese patent application publication No. CN 1673232A) can specifically bind the said polypeptide, indicating that the core polypeptide might comprise epitopes recognized by AD5-10. And subsequent experiments have proved that the said core peptide is the epitope recognized by AD5-10 and other monoclonal antibodies raised by it by using molecular biology, cell biology and Oriented Peptide Array Library (OPAL) techniques; the said core polypeptide is further confirmed to be the epitope of the monoclonal antibody AD5-10 by using polypeptide synthesis technique and genetic engineering site-directed mutagenesis technique. Subsequently, an antigenic peptide comprising this core polypeptide is synthesized in accordance with the amino acid sequence of DR5 molecule and mice are immunized with this antigenic peptide, then the splenocytes of the immunized mice are fused with SP2/0 myeloma cell to obtain the hybridoma cells, then multiple hybridoma cell lines capable of producing monoclonal antibodies which can produce specifically recognize the antigenic peptide (the representative results please refer to FIG. 1) and have tumoricidal activity (the representative results please refer to FIG. 2) are obtained through screening, in which two hybridoma cell lines are named as Adie-1 and Adie-2. Both the hybridoma cell lines were deposited at China General Microbiological Culture Collection Center (CGMCC) on 20 Mar. 2009 with the deposit numbers 2938 and 2939, respectively, of which the classification name is BALB/c mouse hydridoma cell. Then, by utilizing molecular biology and cell biology approaches, it is confirmed that AD5-10 (Chinese patent application publication No. CN1673232A) can also specifically recognize and bind this core peptide sequence (the representative results please refer to FIG. 3). Thus, it is proved that the core peptide sequence comprises the linear epitope recognized by AD5-10. Based on this, the said specific epitope is screened out from the "overlapping" polypeptide pool by using Oriented Peptide Array Library (OPAL) technique (the representative results please refer to FIG. 4). The polypeptides comprising the said epitope and mutant polypeptide of which the amino acid residues on key positions are mutated are synthesized in accordance with the said experimental results, and then the binding information of the polypeptides to AD5-10 is detected. It is found that all the polypeptides comprising the said epitope are capable of binding AD5-10 while the mutant polypeptides of which the amino acid residues on key positions are mutated can not bind AD5-10 (the representative results please refer to FIG. 5). At last, eukaryotic expression vectors expressing the full length wild type DR5 and the full length mutant DR5 comprising the said mutations above are constructed and then, the details that AD5-10 recognizes and binds the epitope is detected by using Western Blotting. It is found that the full length wild type DR5 can recognize AD5-10 and bind the epitope while it is contrary for the full length mutant DR5 comprising the said mutations (the representative results please refer to FIG. 6). The said core peptide obtained according to the present invention and derivatives thereof can be used to develop monoclonal antibodies capable of binding DR5, to screen small molecular compounds capable of binding DR5 and for the treatment of cancers and/or AIDS, to prepare vaccines for the prevention or treatment of cancers and/or AIDS. The nucleotide sequences encoding for the core polypeptide and derivatives thereof according to present invention can be used to prepare the anti-sense nucleotides and small molecular ribonucleotides for the treatment and the prevention of cancers and/or AIDS. The monoclonal antibodies according to present invention can also be used to prepare the anti-tumor and/or anti-AIDS medicaments.

DESCRIPTION OF DRAWINGS

FIGS. 1A and 1C illustrate the binding activity of supernatants of hybridoma cell lines capable of producing corresponding monoclonal antibodies to the antigenic peptide or recombinant DR5 extracellular region protein molecule. FIGS. 1B and 1D illustrate the results of the binding activity of monoclonal antibodies Adie-1 and Adie-2 to the antigenic peptide and recombinant DR5 extracellular region protein molecule at different dilution concentrations.

FIG. 2A demonstrates the morphological characteristics of the cells differently treated under the microscope (40×). FIGS. 2B and 2C show the viability of HCT cells under the different treatment conditions.

FIG. 4: showing the screening and confirmation of the polypeptides comprising the core polypeptide sequence which can be specifically recognized and bound by AD5-10 through Oriented Peptide Array Library technique. These derivative sequences of the core polypeptide mainly distribute in the non-Cysteine-Rich Domain of the N-terminal of the extracellular domain of DR5. The amino acid sequences of these polypeptide derivatives are as follows:

ESALITQQDLAP       (a.a. 1-12)   (SEQ ID No: 3)

ALITQQDLAPQQ       (a.a. 3-14)   (SEQ ID No: 4)

ITQQDLAPQQRA       (a.a. 5-16)   (SEQ ID No: 5)

QQDLAPQQRAAP       (a.a. 7-18)   (SEQ ID No: 6)

Wherein the binding abilities of ALITQQDLAPQQ (a.a.3-14) (SEQ ID No: 4) and ITQQDLAPQQRA (a.a.5-16) (SEQ ID No: 5) to AD5-10 are the strongest (i.e. the antigenicities are the strongest). Thereby the amino acid sequence of the epitope recognized by AD5-10 is determined to be LITQQDLAPQQRA (a.a.4-16) (SEQ ID No: 7). Furthermore, FIG. 4A shows that the shortest amino acid sequence of the epitope recognized by AD5-10 is the core peptide QDLAP (SEQ ID No:1). FIG. 4B shows the results of alanine mutation scan of the said epitope above LITQQDLAPQQRA (a.a.4-16) (SEQ ID No: 7), wherein the thirteen amino acid residues are replaced with Alanine (A) residue in turn. It is found that the binding ability of the epitope and derivatives thereof to AD5-10 is reduced or lost when the tightly adjacent aspartic acid (D) residue, Leucine (L) residue and Alanine (A) residue within the epitope and derivatives thereof are mutated, proving that these three amino acid residues play a key role in this epitope and Leucine (L) residue is vital. Likewise, Leucine (L) residue and Alanine (A) residue of said three amino acid residues play an important role in the processes Adie-1 and Adie-2 recognize the antigenic peptide and bind to it. FIG. 4C shows the construction of permutation arrays aiming at the epitope LITQQDLAPQQRA (a.a.4-16) (SEQ ID No: 7) recognized by AD5-10, wherein every amino acid residue in the said polypeptide sequence is replaced with 20 common amino acid residues in turn. The results prove that the epitopes recognized by AD5-10 comprise the amino acid sequences as represent by the following Formula (I):

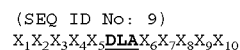
(SEQ ID No: 9)

wherein:

$X_1$ is any amino acid residue, but not required if there is no specification, $X_2$ is any amino acid residue except for Lysine residue, $X_3$ is any amino acid residue, $X_4$ is any amino acid residue, $X_5$ is any amino acid residue, $X_4$ and $X_5$ can be the same or different, $X_6$ is any amino acid residue except for basic or branched-chain amino acid residue, $X_7$ is any amino acid residue except for basic amino acid residue, $X_8$ is any amino acid residue except for basic amino acid residue, $X_7$ and $X_8$ can be the same or different, $X_9$ is any amino acid residue, but not required if there is no specification, and $X_{10}$ is any amino acid residue, but not required if there is no specification.

Figure 5:
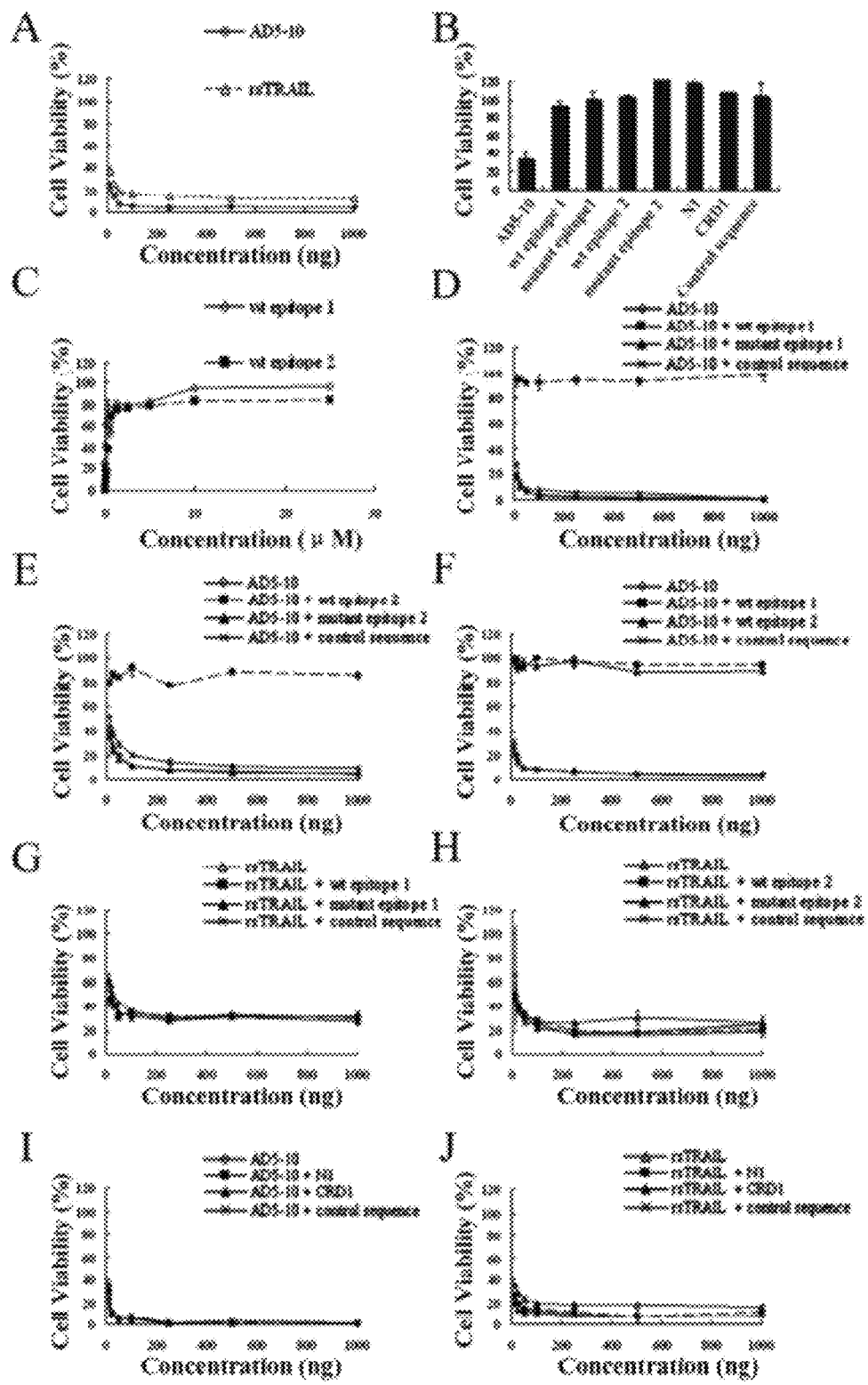

FIG. 5: showing that the synthetic polypeptides comprising the said epitope (please refer to Table 3) bind AD5-10 and can block the tumoricidal activity of AD5-10. FIG. 5A shows the cell survival rate of human T lymphocyte leukemia Jurkat cells after 8 hours treated with AD5-10 and the recombinant soluble TRAIL (rsTRAIL) at different concentrations; FIG. 5B shows the cell survival rate of Jurkat cells after 8 hours treated with AD5-10 (250 ng/ml) and seven synthetic polypeptides; FIG. 5C shows that wild-type epitope 1 (w.t. epitope 1) and wile-type epitope 2 (w.t. epitope 2) at different concentrations can bind to AD5-10 and block their cytotoxicity; FIG. 5D shows that wild-type epitope 1 (w.t. epitope 1, 10 μM) binds to AD5-10 and block its cyctotoxicity, while its corresponding mutant epitope 1 (10 μM) fails to bind to AD5-10; FIG. 5E shows that wild-type epitope 2 (w.t. epitope 2, 10 μM) binds to AD5-10 and block its cyctotoxicity, while its corresponding mutant epitope 2 (10 μM) fails to bind to AD5-10; FIGS. 5G and 5H show that neither the wild-type epitope nor the mutant epitope can block the tumoricidal activity of rsTRAIL. FIGS. 5I and 5J shows that the polypeptides comprising the amino acid residues of the Cysteine-Rich Domain of the extracellular domain of human DR5 can not block the tumoricidal activity of AD5-10 or rsTRAIL.

FIG. 6: showing that AD5-10 can recognize the full length wild-type DR5 molecule and bind to it while can not bind to their mutants of DR5 epitope.

DETAILED DESCRIPTION OF THE INVENTION

Example 1

Determining the Recognition and Binding of the Monoclonal Antibodies Obtained from the Mice Immunized with the Antigenic Peptides to the Antigenic Peptides and DR5 with Enzyme-Linked Immuno Sorbent Assay (ELISA)

The hybridoma culture supernatants or purified antibodies of different numbers are collected, diluted according to a certain proportion and then the ELISA detection is carried out. The specific steps are as follows:
1) Enzyme-linked immuno sorbent assay plates were first coated with the antigenic peptides or recombinant DR5 expressed in prokaryotic systems in an amount of 100 ng/well;
2) The plates were incubated at 37° C. for 1 h with 5% BSA to block nonspecific sites;
3) The plates were then incubated at 37° C. for another 1 h with antibodies of different concentrations;
4) The plates were washed three to five times with PBS/T;
5) The plates were incubated with HRP-conjugated goat anti-mouse IgG secondary antibodies at 37° C. for 1 h;
6) The plates were washed three to five times with PBS/T;
7) The chromogenic substrate was added and then the reaction was stopped by adding 2M sulfuric acid when notable difference appeared and the OD absorbance values were detected.

Figure 1:
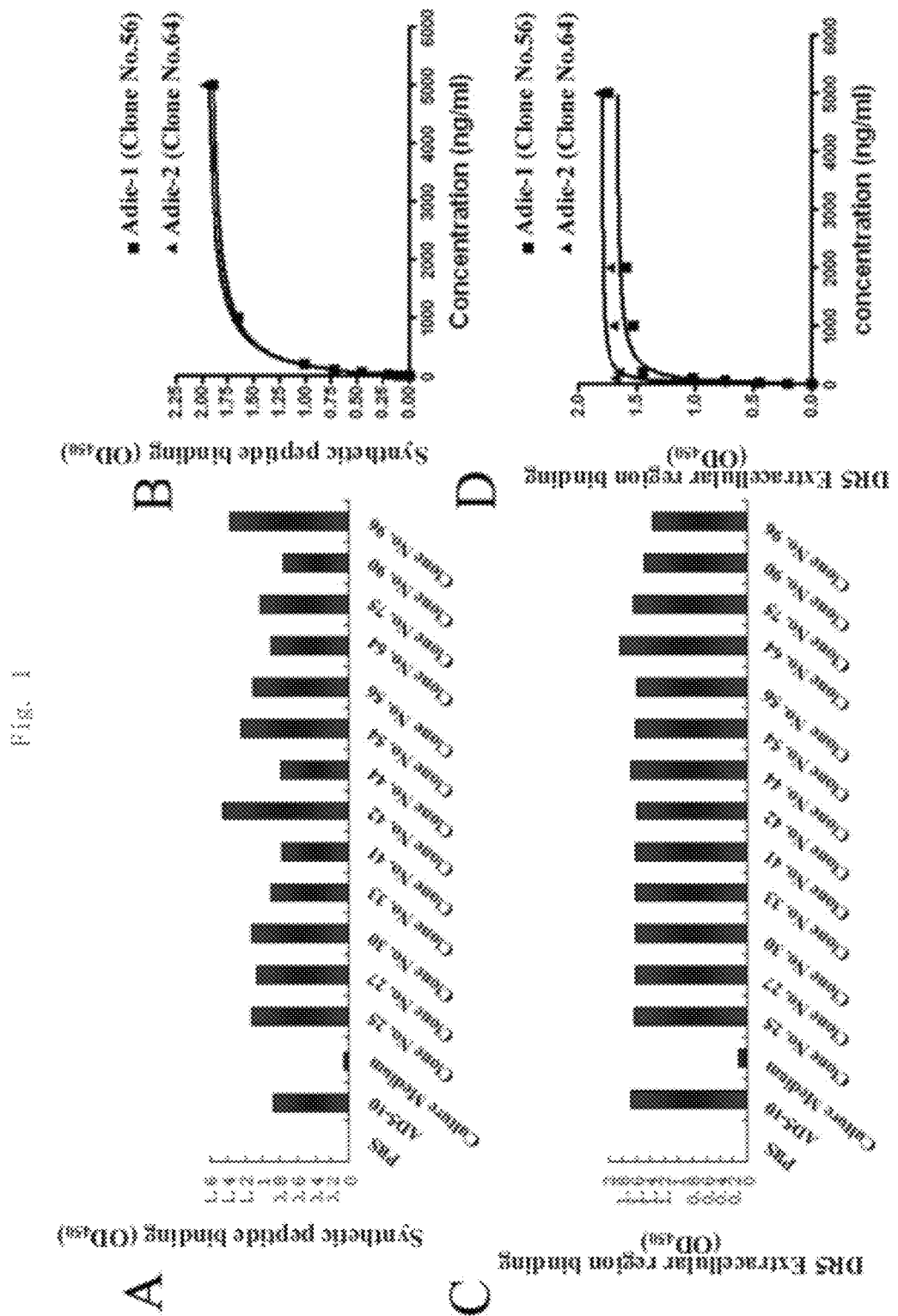
FIG. 1: showing the results of the monoclonal antibodies obtained from the mice immunized with the antigenic peptide having keyhole limpet hemocyanin (KLH) on the N-terminal to recognize and bind the antigenic peptide and DR5.

The results are illustrated in FIG. 1. FIGS. 1A and 1C indicate the binding activity of the supernatants of hybridoma cell lines culture obtained from the mice immunized with the antigenic peptides coupled of keyhole limpet hemocyanin at the N-terminal to the antigenic peptide or recombinant DR5 extracellular region protein molecule. FIGS. 1B and 1D show the binding activity of the monoclonal antibodies Adie-1 (clone No. 56#) and Adie-2 (clone No. 64#) of different concentrations to the antigenic peptides or recombinant DR5 extracellular region protein molecule.

Example 2

The Tumoricidal Activities of TRAIL, AD5-10 and Monoclonal Antibodies Adie-1 and Adie-2 to Human Colon Cancer Cells HCT116

HCT116 cells were treated with TRAIL, AD5-10 and monoclonal antibodies Adie-1 and Adie-2 of different concentrations. The cells were observed under microscope after 24 h and CCK-8 (Dojindo Laboratories, Kumamoto, Japan) was used and the OD values (wavelength 570 nm) were detected 2 h after the reaction. The OD value of the wells having no cells was set to be "0", the Relative cell viability=OD value of treated well/OD value of untreated sample×100%.

Figure 2:
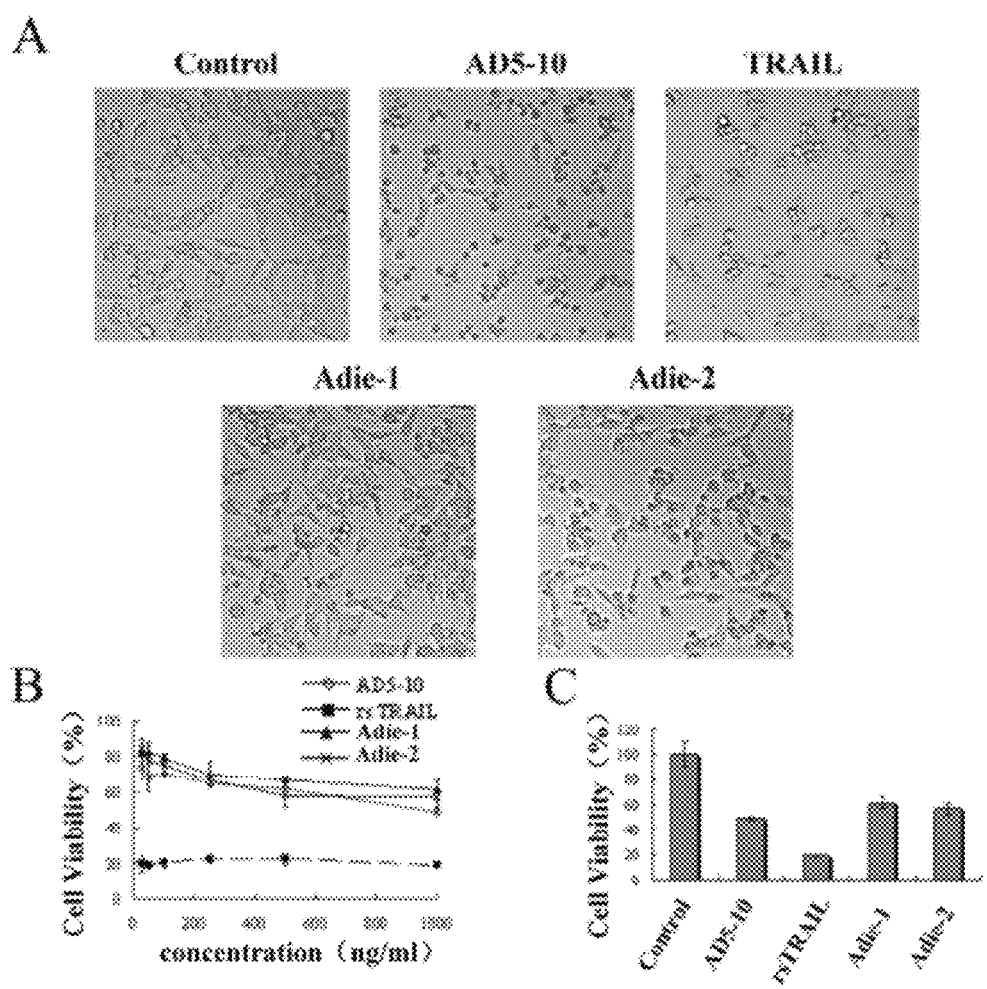
FIG. 2: showing that monoclonal antibodies Adie-1 and Adie-2 have tumoricidal activity to human colon cancer cell HCT116 when compared with TRAIL and AD5-10.

The experimental results were shown in FIG. 2. Apparent morphological changes and cell death characteristics of HCT116 cells treated with TRAIL (500 ng/ml), AD5-10 and monoclonal antibodies Adie-1 (500 ng/ml) and Adie-2 (500 ng/ml) for 8 h were observed under microscope. FIGS. 2B and 2C show that the cell viability of HCT116 cells is notably reduced with the increase of the treatment concentrations under different treatment conditions.

Example 3

Detecting the Ability of TRAIL, AD5-10 and Monoclonal Antibodies Adie-1 and Adie-2 to Activate Caspase Cascade Reaction with Western Blotting Jurkat cells and HCT116 cells in exponential phase were treated with TRAIL (500 ng/ml), AD5-10 (500 ng/ml) and Adie-1 (1 μg/ml) and Adie-2 (1 μg/ml) for 0, 30, 60 min, the cells were collected and lysed, and then separated by SDS-polyacrylamide gel electrophoresis and the proteins in the gel were transferred onto a PVDF membrane, specific antibodies were added to hybrid the proteins, then horseradish peroxidase-conjugated secondary antibody was added, the chromogenic substrate was added definitively.

Figure 3:
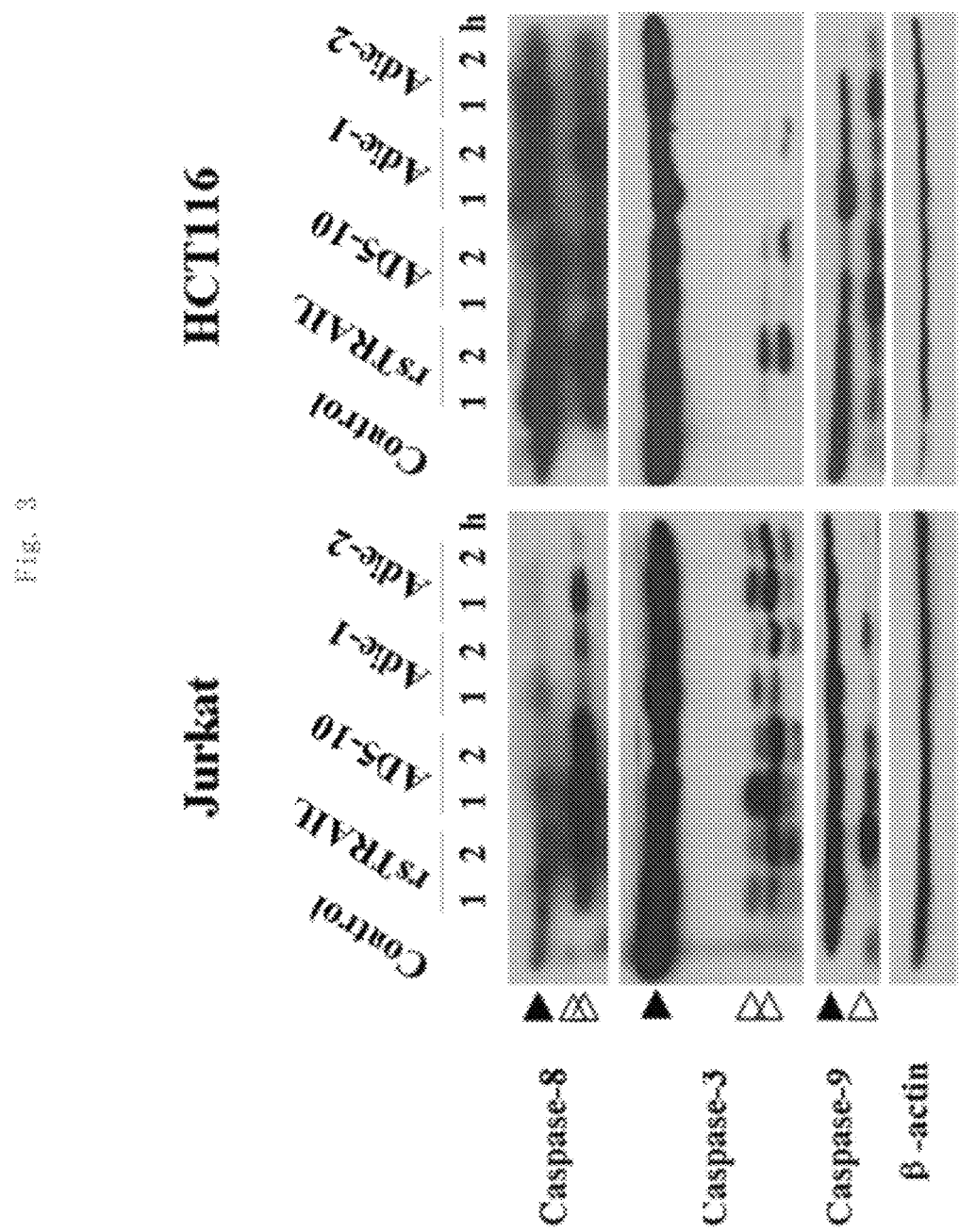
FIG. 3: showing that monoclonal antibodies Adie-1 and Adie-2 also have the capability activating caspase cascade reaction in Jurkat and HCT116 cells when compared with TRAIL and AD5-10.

The experimental results were shown in FIG. 3. Compared to TRAIL and AD5-10, the monoclonal antibodies Adie-1 and Adie-2 can also activate the Caspase Cascade reaction in Jurkat cells and HCT 116 cells.

Example 4

The Screening and Identification of Epitopes and Derivatives Thereof Recognized by AD5-10 with Oriented Peptide Array Library Technique A series of the derivative peptides comprising the core peptide (as shown in Tab. 1 and 2) were synthesized according to the amino acid sequence of human DR5 (NCBI Acc #: NP_671716.1) provided in NCBI protein database. Subsequently, the peptide arrays as said above were spotted on nitrocellulose membranes using an ASP222 SPOT robot workstation (one dot corresponds to one polypeptide of which the concentration is about 5 nmol), the homogenicity of the protein amount was detected with ninhydrin staining before the corresponding detection. The membrane was blocked with 3% BSA in TBS-T solution for 1 h at room temperature and followed by incubation with corresponding specific primary antibodies (the final concentration is 2 μg/ml) at 4° C. over night. The array membrane was then incubated with HRP-conjugated goat anti-mouse polyclonal antibodies for 2 h at room temperature and then chromogenic substrate ECL was added to develop the membrane.

TABLE 1

Derivative polypeptides comprising the core peptide constructed according to the amino acid of human DR5 molecule

| | |
|---|---|
| 1 | ESALITQQDLAP (SEQ ID No:3) |
| 2 | ALITQQDLAPQQ (SEQ ID No:4) |
| 3 | ITQQDLAPQQRA (SEQ ID No:5) |
| 4 | QQDLAPQQRAAP (SEQ ID No:6) |
| 5 | DLAPQQRAAPQQ (SEQ ID No:14) |

TABLE 2

Peptides for alanine mutation scanning array

| | |
|---|---|
| 1 | LITQQDLAPQQRA (SEQ ID No: 7) |
| 2 | AITQQDLAPQQRA (SEQ ID No: 16) |
| 3 | LATQQDLAPQQRA (SEQ ID No: 17) |
| 4 | LIAQQDLAPQQRA (SEQ ID No: 18) |
| 5 | LITAQDLAPQQRA (SEQ ID No: 19) |
| 6 | LITQADLAPQQRA (SEQ ID No: 20) |
| 7 | LITQQALAPQQRA (SEQ ID No: 21) |
| 8 | LITQQDAAPQQRA (SEQ ID No: 22) |
| 9 | LITQQDLAPQQRA (SEQ ID No: 23) |
| 10 | LITQQDLAAQQRA (SEQ ID No: 24) |

TABLE 2-continued

Peptides for alanine mutation scanning array

| | |
|---|---|
| 11 | LITQQDLAPAQRA (SEQ ID No: 25) |
| 12 | LITQQDLAPQARA (SEQ ID No: 26) |
| 13 | LITQQDLAPQQAA (SEQ ID No: 27) |
| 14 | LITQQDLAPQQRA (SEQ ID No: 28) |
| 15 | LITQQDLAPQQRA (SEQ ID No: 7) |

Wherein, the sequences in bold and underlined represent the core sequence of the epitope; the characters in box indicate the mutated amino acid residues.

The experimental results were shown in FIG. 4. AD5-10 can specifically recognize and bind to peptides comprising the core peptide (FIG. 4A). These derivative peptides of the core peptide mainly distribute in the non-Cysteine-Rich Domain in the N-terminal of the extracellular domain of DR5. The amino acid sequences of these peptide derivatives are listed as follows:

```
                                      (SEQ ID No: 3)
            ESALITQQDLAP (a.a. 1-12)

(SEQ ID No: 4)
            ALITQQDLAPQQ (a.a. 3-14)

(SEQ ID No: 5)
            ITQQDLAPQQRA (a.a. 5-16)

(SEQ ID No: 6)
            QQDLAPQQRAAP (a.a. 1-12)
```

Wherein, the binding capabilities to AD5-10 of ALITQQ DLAPQQ (a.a. 3-14) (SEQ ID No: 4) and ITQQ DLAPQQRA (a.a. 5-16) (SEQ ID No: 5) were the strongest (i.e. the antigenicity is the strongest). Thus, the amino acid sequence of the epitope recognized by AD5-10 is determined to be LITQQDLAPQQRA (a.a.4-16) (SEQ ID No: 7). While the shortest amino acid sequence of the epitope recognized by AD5-10 is the core peptide QDLAP (SEQ ID No: 1). As shown in Figure B, an alanine mutation scanning was conducted on the epitope LITQQDLAPQQRA (a.a.4-16) (SEQ ID No: 7) in which the 13 amino acid residues were replaced with Alanine (A) residue in turn. It is found that the binding ability of the epitope and derivatives thereof to AD5-10 is reduced or lost when the tightly adjacent aspartic acid (D) residue, Leucine (L) residue and Alanine (A) residue within the epitope and derivatives thereof are mutated, proving that these three amino acid residues play a key role in this epitope and Leucine (L) residue is vital. Likewise, Leucine (L) residue and Alanine (A) residue of said three amino acid residues play an important role in the processes Adie-1 and Adie-2 recognize the antigenic peptide and bind to it. FIG. 4C shows the construction of permutation arrays aiming at the epitope LITQQDLAPQQRA (a.a.4-16) (SEQ ID No: 7) recognized by AD5-10, wherein every amino acid residue in the said polypeptide sequence is replaced with 20 common amino acid residues in turn. The results prove that the epitopes recognized by AD5-10 comprise the amino acid sequences as represent by the following Formula (I):

(SEQ ID No: 9)

wherein:
$X_1$ is any amino acid residue, but not required if there is no specification,
$X_2$ is any amino acid residue except for Lysine residue,
$X_3$ is any amino acid residue,
$X_4$ is any amino acid residue,
$X_5$ is any amino acid residue, $X_4$ and $X_5$ can be the same or different,
$X_6$ is any amino acid residue except for basic or branched-chain amino acid residue,
$X_7$ is any amino acid residue except for basic amino acid residue,
$X_8$ is any amino acid residue except for basic amino acid residue, $X_7$ and $X_8$ can be the same or different,
$X_9$ is any amino acid residue, but not required if there is no specification, and
$X_{10}$ is any amino acid residue, but not required if there is no specification.

Example 5

Chemically Synthesizing the Peptide Derivatives Comprising the Epitope Associated with Present Invention and Detecting the Ability of them to Bind to AD5-10 and to Block the Tumoricidal Activity of it After the epitope recognized by AD5-10 has been confirmed to be fallen within the scope of the amino acid sequence "LITQQDLAPQQRA (SEQ ID No:7)" by utilizing the peptide arrays, the peptides were chemically synthesized. Simultaneously, the wild type sequences and the peptide derivatives comprising the mutated sequences were constructed so as to further clarify the epitope recognized by AD5-10. It can be learned from the experimental results as described above that the Leucine (L) residue on the fourth position have no function on the binding of AD5-10 and DR5. Thus, this amino acid residue is replaced with a polar, neutral amino acid residue (such as glutamine, Gln) or Alanine (A) so as to increase the water-solubility of the synthetic peptide fragment. The specific information of the peptide synthesis is shown in Table 3:

TABLE 3

| | | Synthetic peptides | | |
|---|---|---|---|---|
| No. | Name | Amino Acid Sequence | M.W. | Purity (%) |
| 1 | wild-type epitope1 | AQITQQDLAPQQRA (SEQ ID No: 29) | 1566.81 | 83.9 |
| 2 | mutant epitope1 | AQITQQD[A][A]PQQRA (SEQ ID No: 30) | 1524.76 | 98.2 |
| 3 | wild-type epitope2 | AITQQDLAPQQRA (SEQ ID No: 31) | 1438.75 | 95 |
| 4 | mutant epitope2 | AITQQD[A][A]PQQRA (SEQ ID No: 32) | 1396.71 | 98.5 |

TABLE 3-continued

| | | Synthetic peptides | | |
|---|---|---|---|---|
| No. | Name | Amino Acid Sequence | M.W. | Purity (%) |
| 5 | N1 | CPPGHHISEDGRDC (SEQ ID No: 33) | 1521.61 | 99 |
| 6 | CRD1 | GQDYSTHWNDLLFCLRC (SEQ ID No: 34) | 2069.91 | 100 |
| 7 | Random peptide | SQRLHTPCFNKMEA (SEQ ID No: 35) | 1660.78 | 99.7 |

Wherein, the sequences in bold and underlined represent the core sequence of the epitope; the characters in box indicate the mutated amino acid residues.

The human lymphocyte leukemia Jurkat cells in exponential phase were seeded in the 96-well plate at the density of $2\times10^4$/well. Then synthetic peptides were sufficiently mixed with AD5-10 according to corresponding concentrations and incubated at 37° C. for 1 h. The mixture was then added to the culture wells containing the tumor cells. CCK-8 agent (Dojindo Laboratories, Kumamoto, Japan) was used and the OD values (wavelength 570 nm) were detected 2 h after the reaction. The OD value of the wells having no cells was set to be "0", the Relative cell viability=OD value of treated well/OD value of untreated sample×100%.

The experimental results were shown in FIG. 5. As shown in FIG. 5A, both AD5-10 and recombinant soluble TRAIL can inhibit the cell viability of human T lymphocyte leukemia Jurkat cells in a dose-dependent manner; As shown in FIG. 5B, compared to AD5-10 (250 ng/ml), seven synthetic epitopes have no effect on the cell viability of Jurkat cells; As shown in FIG. 5C, wild-type epitope 1 (w.t. epitope 1) and wild-type epitope 2 (w.t. epitope 2) of different concentrations can bind to AD5-10 and block its cytotoxicity. As shown in FIG. 5D, wild-type epitope 1 (w.t. epitope 1, 10 μM) can bind to AD5-10 and block its cytotoxicity, while its corresponding mutant epitope 1 (10 μM) cannot bind to AD5-10; As shown in FIG. 5E, wild-type epitope 2 (w.t. epitope 2, 10 μM) can bind to AD5-10 and block its cytotoxicity, while its corresponding mutant epitope 2 (10 μM) cannot bind to AD5-10. FIGS. 5G and 5H show that neither the wild-type epitope nor the mutant epitope can block the tumoricidal activity of rsTRAIL. FIGS. 5I and 5J shows that the polypeptides comprising the amino acid residues of the Cysteine-Rich Domain of the extracellular domain of human DR5 can not block the tumoricidal activity of AD5-10 or rsTRAIL.

Example 6

Detecting the Binding Ability of AD5-10 to Wild-Type DR5 in Full Length and Mutant DR5 in Full Length with Western Blotting Technique The eukaryotic expression vector expressing the wild-type DR5 in full length carrying a 3× FLAGE tag and the eukaryotic expression vector expressing the mutant DR5 in full length carrying a 3× FLAG tag were constructed and transfected into 293T-17 cells. The cells were harvested and lysed, and the cell lysates were separated by SDS-polyacrylamide gel electrophoresis, and then the proteins in the gel were transferred onto a PVDF membrane (GE Healthcare), specific antibodies were added to hybrid the proteins, then horseradish peroxidase-conjugated secondary antibody was added, the chromogenic substrate was added definitively to develop the membrane.

As shown in FIG. 6, AD5-10 can recognize the full length wild-type DR5 molecule and bind to it while can not bind to their mutants of DR5 epitope.

```
                        SEQUENCE LISTING

<160> NUMBER OF SEQ ID NOS: 35

<210> SEQ ID NO 1
<211> LENGTH: 5
<212> TYPE: PRT
<213> ORGANISM: artificial
<220> FEATURE:
<223> OTHER INFORMATION: Antigenic determinants recognized by the mouse
      anti-human death receptor DR5 monoclonal antibody AD5-10

<400> SEQUENCE: 1

Gln Asp Leu Ala Pro
1               5

<210> SEQ ID NO 2
<211> LENGTH: 15
<212> TYPE: DNA
<213> ORGANISM: artificial
<220> FEATURE:
<223> OTHER INFORMATION: The degenerate sequence encoding for Seq ID
      NO. 1
<220> FEATURE:
<221> NAME/KEY: misc_feature
<222> LOCATION: (3)..(3)
<223> OTHER INFORMATION: r is a or g
<220> FEATURE:
<221> NAME/KEY: misc_feature
<222> LOCATION: (6)..(6)
<223> OTHER INFORMATION: y is t or c
<220> FEATURE:
<221> NAME/KEY: misc_feature
<222> LOCATION: (9)..(9)
<223> OTHER INFORMATION: n is a, t, g or c
<220> FEATURE:
<221> NAME/KEY: misc_feature
<222> LOCATION: (12)..(12)
<223> OTHER INFORMATION: n is a, t, g or c
<220> FEATURE:
<221> NAME/KEY: misc_feature
<222> LOCATION: (15)..(15)
<223> OTHER INFORMATION: n is a, t, g or c
<220> FEATURE:
<221> NAME/KEY: misc_feature
<222> LOCATION: (15)..(15)
<223> OTHER INFORMATION: n is a, t, g or c

<400> SEQUENCE: 2
cargayctng cnccn                                                         15

<210> SEQ ID NO 3
<211> LENGTH: 12
<212> TYPE: PRT
<213> ORGANISM: artificial
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 3

Glu Ser Ala Leu Ile Thr Gln Gln Asp Leu Ala Pro
1               5                   10

<210> SEQ ID NO 4
<211> LENGTH: 12
<212> TYPE: PRT
<213> ORGANISM: artificial
```

-continued

```
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 4

Ala Leu Ile Thr Gln Gln Asp Leu Ala Pro Gln Gln
1               5                   10

<210> SEQ ID NO 5
<211> LENGTH: 12
<212> TYPE: PRT
<213> ORGANISM: artificial
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 5

Ile Thr Gln Gln Asp Leu Ala Pro Gln Gln Arg Ala
1               5                   10

<210> SEQ ID NO 6
<211> LENGTH: 12
<212> TYPE: PRT
<213> ORGANISM: artificial
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 6

Gln Gln Asp Leu Ala Pro Gln Gln Arg Ala Ala Pro
1               5                   10

<210> SEQ ID NO 7
<211> LENGTH: 13
<212> TYPE: PRT
<213> ORGANISM: artificial
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 7

Leu Ile Thr Gln Gln Asp Leu Ala Pro Gln Gln Arg Ala
1               5                   10

<210> SEQ ID NO 8
<211> LENGTH: 18
<212> TYPE: PRT
<213> ORGANISM: artificial
<220> FEATURE:
<223> OTHER INFORMATION: Extended sequence of SEQ ID NO. 1 which extends
      from the N-terminal of the said amino acid sequence to the
      C-terminal of the amino acid sequence in accordance with the amino
      acid sequence of DR5

<400> SEQUENCE: 8

Glu Ser Ala Leu Ile Thr Gln Gln Asp Leu Ala Pro Gln Gln Arg Ala
1               5                   10                  15

Ala Pro

<210> SEQ ID NO 9
```

```
<211> LENGTH: 13
<212> TYPE: PRT
<213> ORGANISM: artificial
<220> FEATURE:
<223> OTHER INFORMATION: formula
<220> FEATURE:
<221> NAME/KEY: site
<222> LOCATION: (1)..(1)
<223> OTHER INFORMATION: present or absent, could be any amino acid
      residue
<220> FEATURE:
<221> NAME/KEY: site
<222> LOCATION: (2)..(2)
<223> OTHER INFORMATION: could be any amino acid residue except for
      Lysine residue
<220> FEATURE:
<221> NAME/KEY: site
<222> LOCATION: (3)..(3)
<223> OTHER INFORMATION: could be any amino acid residue
<220> FEATURE:
<221> NAME/KEY: site
<222> LOCATION: (3)..(4)
<223> OTHER INFORMATION: could be any amino acid residue
<220> FEATURE:
<221> NAME/KEY: site
<222> LOCATION: (5)..(5)
<223> OTHER INFORMATION: could be any amino acid residue, could be the
      same as or different from X4
<220> FEATURE:
<221> NAME/KEY: site
<222> LOCATION: (5)..(5)
<223> OTHER INFORMATION: could be any amino acid residue, could be the
      same as or different from X4
<220> FEATURE:
<221> NAME/KEY: site
<222> LOCATION: (9)..(9)
<223> OTHER INFORMATION: could be any amino acid residue except for
      basic or branched-chain amino acid residue
<220> FEATURE:
<221> NAME/KEY: site
<222> LOCATION: (10)..(10)
<223> OTHER INFORMATION: could be any amino acid residue except for
      basic amino acid residue
<220> FEATURE:
<221> NAME/KEY: site
<222> LOCATION: (11)..(11)
<223> OTHER INFORMATION: could be any amino acid residue except for
      basic amino acid residue, could be the same as or different from
      X7
<220> FEATURE:
<221> NAME/KEY: site
<222> LOCATION: (12)..(13)
<223> OTHER INFORMATION: present or absent, could be any amino acid
      residue

<400> SEQUENCE: 9

Xaa Xaa Xaa Xaa Xaa Asp Leu Ala Xaa Xaa Xaa Xaa Xaa
1               5                   10

<210> SEQ ID NO 10
<211> LENGTH: 12
<212> TYPE: PRT
<213> ORGANISM: artificial
<220> FEATURE:
<223> OTHER INFORMATION: derivative polypeptide 1 comprising the core
      peptide constructed according to the amino acid sequence of human
      DR5 molecule

<400> SEQUENCE: 10

Glu Ser Ala Leu Ile Thr Gln Gln Asp Leu Ala Pro
1               5                   10

<210> SEQ ID NO 11
<211> LENGTH: 12
<212> TYPE: PRT
```

```
<213> ORGANISM: artificial
<220> FEATURE:
<223> OTHER INFORMATION: derivative polypeptide 2 comprising the core
      peptide constructed according to the amino acid sequence of human
      DR5 molecule

<400> SEQUENCE: 11

Ala Leu Ile Thr Gln Gln Asp Leu Ala Pro Gln Gln
1               5                   10

<210> SEQ ID NO 12
<211> LENGTH: 12
<212> TYPE: PRT
<213> ORGANISM: artificial
<220> FEATURE:
<223> OTHER INFORMATION: derivative polypeptide 3 comprising the core
      peptide constructed according to the amino acid sequence of human
      DR5 molecule

<400> SEQUENCE: 12

Ile Thr Gln Gln Asp Leu Ala Pro Gln Gln Arg Ala
1               5                   10

<210> SEQ ID NO 13
<211> LENGTH: 12
<212> TYPE: PRT
<213> ORGANISM: artificial
<220> FEATURE:
<223> OTHER INFORMATION: derivative polypeptide 4 comprising the core
      peptide constructed according to the amino acid sequence of human
      DR5 molecule

<400> SEQUENCE: 13

Gln Gln Asp Leu Ala Pro Gln Gln Arg Ala Ala Pro
1               5                   10

<210> SEQ ID NO 14
<211> LENGTH: 12
<212> TYPE: PRT
<213> ORGANISM: artificial
<220> FEATURE:
<223> OTHER INFORMATION: derivative polypeptide 5 comprising the core
      peptide constructed according to the amino acid sequence of human
      DR5 molecule

<400> SEQUENCE: 14

Asp Leu Ala Pro Gln Gln Arg Ala Ala Pro Gln Gln
1               5                   10

<210> SEQ ID NO 15
<211> LENGTH: 13
<212> TYPE: PRT
<213> ORGANISM: artificial
<220> FEATURE:
<223> OTHER INFORMATION: wild type peptide for alanine mutation scanning
      array

<400> SEQUENCE: 15

Leu Ile Thr Gln Gln Asp Leu Ala Pro Gln Gln Arg Ala
1               5                   10

<210> SEQ ID NO 16
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
```

-continued

```
<222> LOCATION: (1)..(1)
<223> OTHER INFORMATION: L is mutated to A

<400> SEQUENCE: 16

Ala Ile Thr Gln Gln Asp Leu Ala Pro Gln Gln Arg Ala
1               5                   10

<210> SEQ ID NO 17
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (2)..(2)
<223> OTHER INFORMATION: I is mutated to A

<400> SEQUENCE: 17

Leu Ala Thr Gln Gln Asp Leu Ala Pro Gln Gln Arg Ala
1               5                   10

<210> SEQ ID NO 18
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (3)..(3)
<223> OTHER INFORMATION: T is mutated to A

<400> SEQUENCE: 18

Leu Ile Ala Gln Gln Asp Leu Ala Pro Gln Gln Arg Ala
1               5                   10

<210> SEQ ID NO 19
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (4)..(4)
<223> OTHER INFORMATION: Q is mutated to A

<400> SEQUENCE: 19

Leu Ile Thr Ala Gln Asp Leu Ala Pro Gln Gln Arg Ala
1               5                   10

<210> SEQ ID NO 20
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (5)..(5)
<223> OTHER INFORMATION: Q is muated to A

<400> SEQUENCE: 20

Leu Ile Thr Gln Ala Asp Leu Ala Pro Gln Gln Arg Ala
1               5                   10

<210> SEQ ID NO 21
<211> LENGTH: 13
```

```
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (6)..(6)
<223> OTHER INFORMATION: D is mutated to A

<400> SEQUENCE: 21

Leu Ile Thr Gln Gln Ala Leu Ala Pro Gln Gln Arg Ala
1               5                   10

<210> SEQ ID NO 22
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (7)..(7)
<223> OTHER INFORMATION: L is mutated to A

<400> SEQUENCE: 22

Leu Ile Thr Gln Gln Asp Ala Ala Pro Gln Gln Arg Ala
1               5                   10

<210> SEQ ID NO 23
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (8)..(8)
<223> OTHER INFORMATION: A is muated to L

<400> SEQUENCE: 23

Leu Ile Thr Gln Gln Asp Leu Leu Pro Gln Gln Arg Ala
1               5                   10

<210> SEQ ID NO 24
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (9)..(9)
<223> OTHER INFORMATION: P is mutated to A

<400> SEQUENCE: 24

Leu Ile Thr Gln Gln Asp Leu Ala Ala Gln Gln Arg Ala
1               5                   10

<210> SEQ ID NO 25
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (10)..(10)
<223> OTHER INFORMATION: Q is mutated to A

<400> SEQUENCE: 25
```

```
Leu Ile Thr Gln Gln Asp Leu Ala Pro Ala Gln Arg Ala
1               5                   10

<210> SEQ ID NO 26
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (11)..(11)
<223> OTHER INFORMATION: Q is mutated to A

<400> SEQUENCE: 26

Leu Ile Thr Gln Gln Asp Leu Ala Pro Gln Ala Arg Ala
1               5                   10

<210> SEQ ID NO 27
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (12)..(12)
<223> OTHER INFORMATION: R is mutated to A

<400> SEQUENCE: 27

Leu Ile Thr Gln Gln Asp Leu Ala Pro Gln Gln Ala Ala
1               5                   10

<210> SEQ ID NO 28
<211> LENGTH: 13
<212> TYPE: PRT
<213> ORGANISM: artificial
<220> FEATURE:
<223> OTHER INFORMATION: peptide for alanine mutation scanning array
<220> FEATURE:
<221> NAME/KEY: site
<222> LOCATION: (13)..(13)
<223> OTHER INFORMATION: A is mutated to L

<400> SEQUENCE: 28

Leu Ile Thr Gln Gln Asp Leu Ala Pro Gln Gln Arg Leu
1               5                   10

<210> SEQ ID NO 29
<211> LENGTH: 14
<212> TYPE: PRT
<213> ORGANISM: artificial
<220> FEATURE:
<223> OTHER INFORMATION: wild type epitope 1

<400> SEQUENCE: 29

Ala Gln Ile Thr Gln Gln Asp Leu Ala Pro Gln Gln Arg Ala
1               5                   10

<210> SEQ ID NO 30
<211> LENGTH: 14
<212> TYPE: PRT
<213> ORGANISM: artificial
<220> FEATURE:
<223> OTHER INFORMATION: mutant epitope 1

<400> SEQUENCE: 30

Ala Gln Ile Thr Gln Gln Asp Ala Ala Pro Gln Gln Arg Ala
1               5                   10
```

```
<210> SEQ ID NO 31
<211> LENGTH: 13
<212> TYPE: PRT
<213> ORGANISM: artificial
<220> FEATURE:
<223> OTHER INFORMATION: wild type epitope 2

<400> SEQUENCE: 31

Ala Ile Thr Gln Gln Asp Leu Ala Pro Gln Gln Arg Ala
1               5                   10

<210> SEQ ID NO 32
<211> LENGTH: 13
<212> TYPE: PRT
<213> ORGANISM: artificial
<220> FEATURE:
<223> OTHER INFORMATION: mutant epitope 2

<400> SEQUENCE: 32

Ala Ile Thr Gln Gln Asp Ala Ala Pro Gln Gln Arg Ala
1               5                   10

<210> SEQ ID NO 33
<211> LENGTH: 14
<212> TYPE: PRT
<213> ORGANISM: artificial
<220> FEATURE:
<223> OTHER INFORMATION: N1

<400> SEQUENCE: 33

Cys Pro Pro Gly His His Ile Ser Glu Asp Gly Arg Asp Cys
1               5                   10

<210> SEQ ID NO 34
<211> LENGTH: 17
<212> TYPE: PRT
<213> ORGANISM: artificial
<220> FEATURE:
<223> OTHER INFORMATION: CDR1

<400> SEQUENCE: 34

Gly Gln Asp Tyr Ser Thr His Trp Asn Asp Leu Leu Phe Cys Leu Arg
1               5                   10                  15

Cys

<210> SEQ ID NO 35
<211> LENGTH: 14
<212> TYPE: PRT
<213> ORGANISM: artificial
<220> FEATURE:
<223> OTHER INFORMATION: control sequence

<400> SEQUENCE: 35

Ser Gln Arg Leu His Thr Pro Cys Phe Asn Lys Met Glu Ala
1               5                   10
```

The invention claimed is:

1. A polypeptide consisting of the amino acid sequence of SEQ ID No: 1.

2. A nucleotide sequence consisting of the sequence of SEQ ID No: 2 encoding for the polypeptide of claim 1, wherein N is selected from A, T, C or G.

3. A method of preparing monoclonal antibodies that bind to DR5 comprising cultivating a hybridoma, which was produced by immunizing an animal with the polypeptide of claim 1, and recovering said antibodies.

* * * * *